United States Patent [19]

Karlson

[11] 4,315,812
[45] Feb. 16, 1982

[54] APPARATUS FOR CONTINUOUS ELECTROCHROMATOGRAPHIC SEPARATION

[76] Inventor: Eskil L. Karlson, 4634 State St., Erie, Pa. 16509

[21] Appl. No.: 154,065

[22] Filed: May 28, 1980

[51] Int. Cl.³ .................... G01N 27/26; G01N 27/30
[52] U.S. Cl. ........................ 204/299 R; 204/180 R; 204/180 G; 422/70
[58] Field of Search .......... 204/299 R, 180 R, 180 G; 422/70; 23/232 C

[56] References Cited

U.S. PATENT DOCUMENTS

| | | | |
|---|---|---|---|
| 2,555,487 | 6/1951 | Haugaard et al. | 204/299 R X |
| 3,450,624 | 6/1969 | Natelson | 204/299 R |
| 3,458,427 | 7/1969 | Strickler | 204/299 R |
| 3,479,265 | 11/1969 | Elevitch | 204/299 R X |
| 3,519,549 | 7/1970 | Grassmann et al. | 204/299 R |
| 3,782,078 | 1/1974 | Jerpe | 55/197 |
| 3,847,773 | 11/1974 | Snyder | 204/299 R X |
| 4,148,703 | 4/1979 | Trop et al. | 204/299 R X |

*Primary Examiner*—Arnold Turk
*Attorney, Agent, or Firm*—Ralph Hammar

[57] ABSTRACT

An apparatus that performs a continuous separation of and the purification of chemical compounds by employing both the phenomena of electrophoresis and chromatography or electrophoresis alone, dependent on the material to be separated. The material to be separated has laminar flow through a chromatographic bed while subjected to an electric field from opposite side edges. The differences in molecular weight or density cause a difference in rate of flow of the components of the chemical compound so the chemical compounds have different lateral movements under the influence of the electric field and are physically separated at the outlet end of the bed.

3 Claims, 4 Drawing Figures

U.S. Patent  Feb. 16, 1982  4,315,812
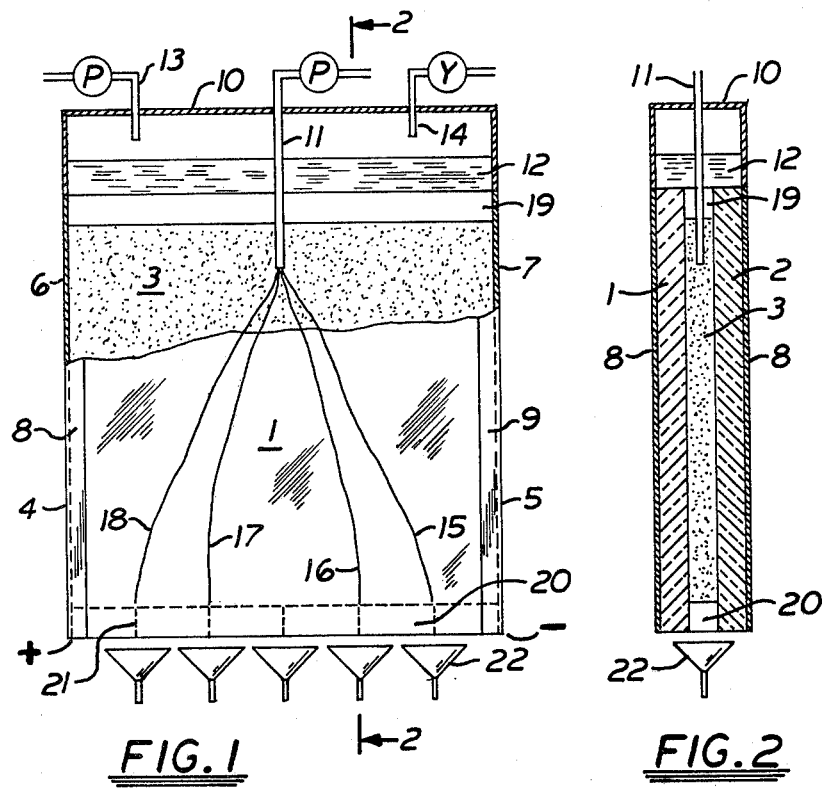
FIG. 1
FIG. 2
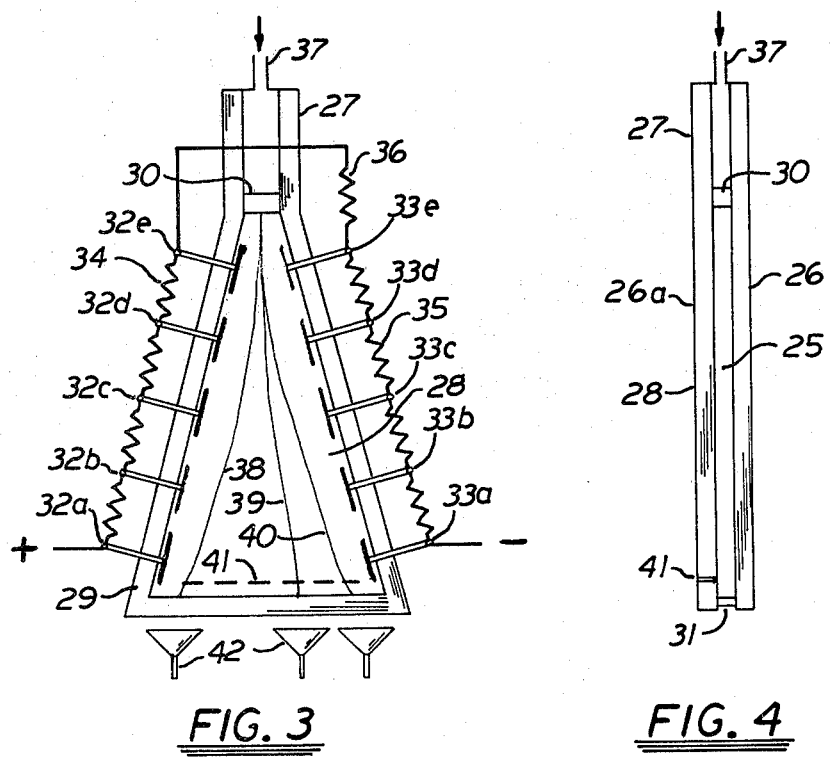
FIG. 3
FIG. 4

APPARATUS FOR CONTINUOUS ELECTROCHROMATOGRAPHIC SEPARATION

This invention is an apparatus for separating mixtures of chemical compounds into their components. In a preferred form the apparatus is made up of two glass sheets on the order of 25 centimeters wide by 50 centimeters long. Between the sheets lies a bed of approximately 5 mm. of filter. This filter could be any one of many filters used in chromatographic columns such as, for example, the polyacrylamide gels. When the chromatographic effect is not relied on, any of the filters used for electrophoresis, such as glass beads, may be used.

In the drawing,

FIG. 1 is a plan view of a preferred form of apparatus,

FIG. 2 is a section on line 2—2 of FIG. 1,

FIG. 3 is a plan view of a modification which eliminates the need for an eluent, and FIG. 4 is an edge elevation of FIG. 3.

Referring to FIG. 1, a sandwich of rectangular glass sheets 1, 2 on opposite sides of a bed 3 of filter material is supported on its long sides by two metal channels 4, 5 with webs 6, 7 that are in contact with the filter between the glass and with flanges 8, 9 that overlap the outer edge faces of the glass. The top edges of the glass are enclosed by a box header or manifold 10 to produce a means of introducing the sample to be separated and the eluent which carries the sample down through the filter.

The sample is pumped into the filter through lines 11, 12 at a single point in the top center of the filter. A layer of eluent is pumped in through line 13 over the total area of the filter at the top end and maintained at a constant liquid level. Liquid level controls are well-known and need not be illustrated. The pressure of both sample and eluent is nearly the same, the sample pressure being only about one-half pound higher to produce the required flow. The pressure on the eluent is held constant by an inert gas fed into the header through control valve 14. The eluent is preferably a liquid in which the sample is soluble.

The eluent and the sample dissolved therein flow down through the filter bed 3 at a rate determined by the pressure and temperature and by molecular weights or densities of the components. The heavier components move slower than the lighter components. The flow is laminar and nonturbulent in the nature of diffusion. The electric field from the voltage applied to channels 4, 5 also has different electrophoretic effects on the different components. In electrophoresis, charged molecules are propelled through a media by an electric field. In this invention the electrical force is at right angles to the direction the sample is moving. The sample will move from the top to out the bottom in a straight line when there is no electric field across its path. When a current is sent across the sample path, the changed molecules will separate from their paths by their different electrophoretic mobilities as indicated by lines 15, 16, 17, 18. Variations in the filter buffer eluent and charge make it possible to separate molecules not only according to charge, but also according to their molecular weights, isoelectric point and biospecific affinity. Samples can be collected along the lower edge of the glass sandwich. The filter medium is kept in place at the top and bottom by fluid transfusable strips 19, 20.

The bottom strip 20 may be provided with slots 21 registering with funnels 22 for collecting the separated components. The lines 15, 16, 17, 18 each indicate a flow path for a different chemical component of a sample being tested at a particular temperature and pressure. The flow paths are unique for the particular components of the sample. By moving a slotted strip 20 along the bottom, it is possible to precisely align one of the flow paths with a particular slot (or with a group of slots if the flow path is broad) which will direct the output of the selected flow path into a particular one of the collectors 22. By employing both the action of chromatography and electrophoresis, a system can be tailored for a specific separation problem that may not be possible by either method.

When high flow with good separation is required or when a high voltage and current flow is reqired, such as in a production plant where many gallons of material are to be separated per minute, cooling must be employed. The outer side of the glass plates 1, 2 and of the side electrodes 4, 5 may be water jacketed, and the water jackets may assist in reenforcing the glass which is subject to considerable outward hydrostatic pressure from the eluent and sample. The plates 1, 2 may be made of sheet metal with a thin coating of glass or porcelain enamel.

In FIGS. 3 and 4 is shown a modification in which the eluent may be eliminated. A preferred form of this apparatus comprises a sandwich of a bed of filter medium 25 between spaced plates 26, 26a of glass or other suitable material, each having a generally rectangular section 27 at the upper end which merges into the upper end of a triangular section 28. The glass plates are bounded by a suitable framework 29 which supports the plates in spaced relation and seals the peripheral edges beween the plates so as to retain liquid and a bed of filter medium 25 such as used for chromatography of electrophoresis. The frame 29 may also include water jackets for cooling and reenforcing the glass. The details of the frame are not shown. At the upper end of the triangular section 28 of the plates is a filter retaining means such as a screen 30. A similar filter retaining means 31 is located at the lower end of the triangular section. Adjacent the outermost edges of the filter medium 25 are a series of electrodes $32a$–$32e$ and $33a$–$33e$ respectively connected to the positive and negative terminals of a voltage source. Resistors 34 respectively connected between adjacent electrodes $32a$–$32e$ and resistors 35 respectively connected between adjacent resistors $33a$–$33e$ and a resistor connected from electrode $32e$ to electrode $33e$ divide the voltage appearing across opposite electrodes. The full voltage appears across the lowermost pair of electrodes $32a$, $33a$ and the smallest voltage appears across the uppermost pair of electrodes $32e$, $33e$. By way of example, the voltage between terminals $32a$ and $33a$ might be from 200 to 2000 volts, the resistor 36 might be 1 megohm and the other resistors might be 100K each.

The fluid to be separated enters under pressure at inlet 37 and flows down through the space between the glass plates 26, 26a. The filter bed between the plates slows down the flow of the individual components at rates which differ in accordance with the molecular weights of the components. The flow is laminar and nonturbulent, in the nature of diffusion. At the same time, the liquid between the plates is being subjected to electric fields between the electrodes $32a$–$32e$ and $33a$–$33e$ producing a sideways movement proportional to the electric field and the electrophoretic properties of the components. The net result is that when the liquid from the inlet 37 has reached steady state flow, the components of the liquid will flow along lines 38, 39, 40 and can be collected in collectors beneath the screen 31.

In order to identify and calibrate the materials, a coloring solution having a particular affinity for one of the components may be injected through a slot 41 in plate 46 which delivers coloring solution across the width of the column. The slot 41 is close to the outlet end where the different components of the incoming liquid have been separated. By injecting the coloring material as dye through slot 41 and noticing where liquid of that color flows through the outlet, it is possible to precisely locate the discharge point for the separated component for which the dye has a particular affinity and to shift one of the collectors 42 so as to collect only that single component. By repeating the process with different dyes, other components may be identified and collected.

As was the case with the FIGS. 1 and 2 construction, water jacketing may be used to maintain constant temperature of the liquid flowing through the filter bed. In the separation of blood plasma a temperature range of from 4° C. to 80° C. must be kept. This apparatus can also separate gases in the same manner as is used to separate samples in solutions.

In the prior art, U.S. Pat. No. 3,503,712 discloses a chromatograph device with the flow between glass plates. There is no concurrent use of electrophoresis.

An article "Automated Elution Electrophoresis: a Potential Clinical Tool", Clinical Chemistry Vol. 21, No. 9, 1975, page 1217, suggests a chromatographic column with an electric field applied in the direction of flow.

U.S. Pat. No. 3,782,078 suggests a chromatographic column with an electric field applied radially outward from a wire at the axis of the column.

The prior art does not show separation by laminar flow longitudinally through a filter bed while subject to an electric field in the plane of the flow and crosswise to the direction of flow.

I claim:

1. An apparatus for continuous molecular separation within a gas or liquid comprising opposed plates of insulation material defining an elongated flattened passageway with an inlet at one end and an outlet at the other end, a bed of glass beads or chromatographic filter material filling said passageway, a series of a plurality of pairs of electrodes, each pair having electrodes on opposite edges of said passageway for producing an edgewise electric charge across the filter material between said plates for effecting lateral movement of the molecular components relative to a flow of fluid in said passageway towards said outlet, said pairs of electrodes being spaced from each other along the length of the passageway, means for supplying a different voltage to each of said pairs of electrodes, and means for introducing into the inlet fluid having components of different molecular weights, size and/or polarity.

2. The apparatus of claim 1 in which the plates define a passageway which increases in width from the inlet toward the outlet and is wider at the outlet than at the inlet.

3. The apparatus of claim 1 having a slot adjacent the outlet through which a coloring solution having a particular affinity for one of said components may be injected across the width of the passageway and across the flow of the sample before it exits so the exit position of said one component may be identified.

* * * * *